United States Patent [19]

Palmius

[11] 4,004,578
[45] Jan. 25, 1977

[54] EXPENDABLE ELECTRO-CARDIOGRAPH ELECTRODE

[75] Inventor: Kjell Hubert Palmius, Spanga, Sweden

[73] Assignee: Salve S.A., Fribourg, Switzerland

[22] Filed: May 14, 1975

[21] Appl. No.: 577,405

[30] Foreign Application Priority Data

Sept. 10, 1974 Sweden .................... 7411404
Jan. 22, 1975 Sweden .................... 7500659

[52] U.S. Cl. .................. 128/2.06 E; 128/2.1 E;
128/416; 128/DIG. 4; 29/629; 29/630 R
[51] Int. Cl.² .............................. A61B 5/04
[58] Field of Search ...... 128/2.06 E, 2.1 E, DIG. 4,
128/404, 410, 411, 416–418; 29/629, 630 R

[56] References Cited

UNITED STATES PATENTS

| | | | |
|---|---|---|---|
| 3,085,577 | 4/1963 | Berman et al. | 128/418 |
| 3,151,619 | 10/1964 | Sullivan | 128/417 |
| 3,505,993 | 4/1970 | Lewes et al. | 128/2.06 E |
| 3,677,268 | 7/1972 | Reeves | 128/417 |
| 3,720,209 | 3/1973 | Bolduc | 128/2.06 E |
| 3,776,228 | 12/1973 | Semler | 128/2.06 E |
| 3,831,589 | 8/1974 | Deering et al. | 128/2.1 E |

FOREIGN PATENTS OR APPLICATIONS

| | | | |
|---|---|---|---|
| 2,064,781 | 12/1970 | Germany | 128/2.06 E |
| 264,608 | 3/1970 | U.S.S.R. | 128/2.1 E |

Primary Examiner—Robert W. Michell
Assistant Examiner—Lee S. Cohen

[57] ABSTRACT

An expendable electrode for electro-cardiographs comprising a thin metallic carrier member coated on the surface to be applied to the skin with an adhesive and having a plurality of metallic contact spikes projecting from the coated surface which spikes are devised to penetrate into the skin. The coated and spiked surface is covered by at least one pull-off foil protecting same together with the spikes against environmental influences. On the carrier member, a transverse upwardly directed flange is provided for attachment to an electrocardiographic apparatus. A method of manufacturing the expandable electrode according to the invention is also disclosed.

19 Claims, 2 Drawing Figures

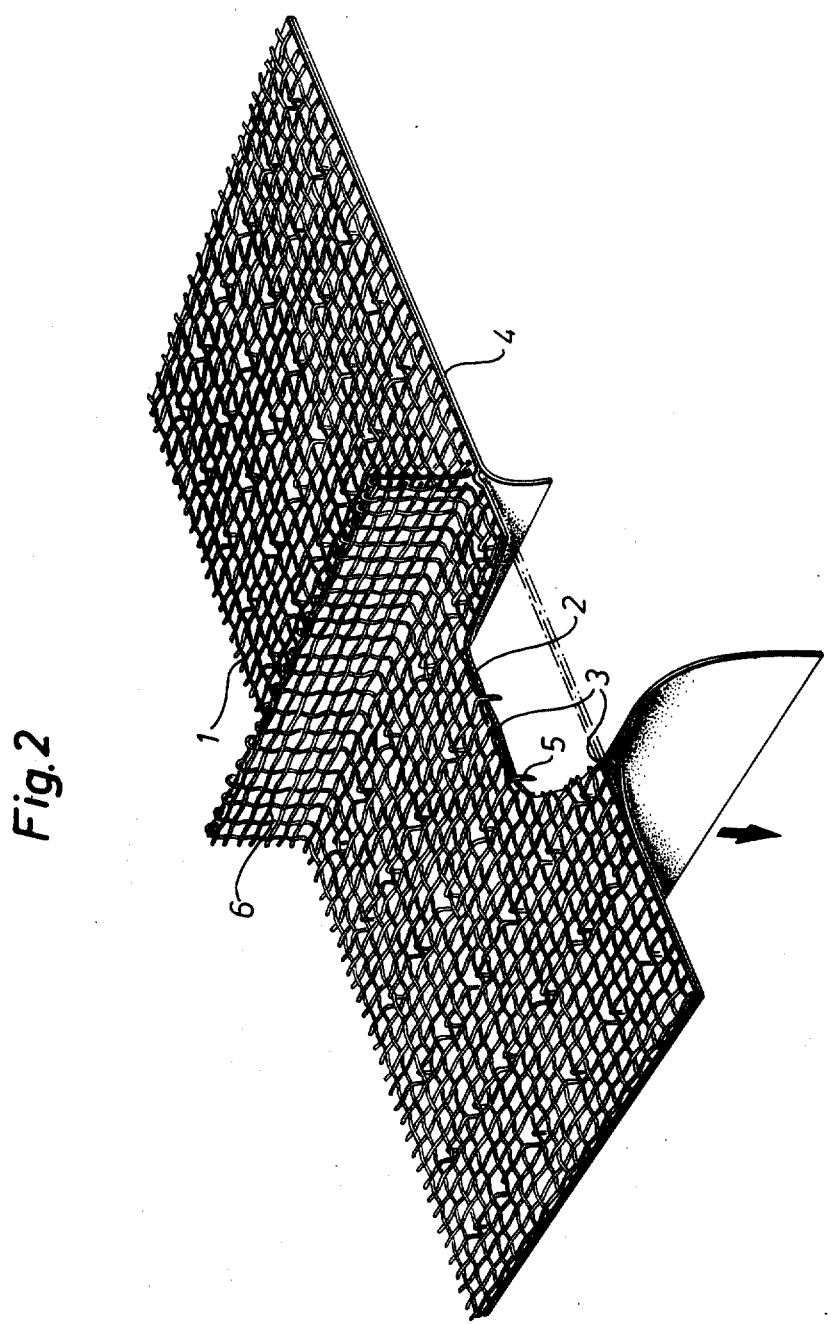

EXPENDABLE ELECTRO-CARDIOGRAPH ELECTRODE

BACKGROUND OF THE INVENTION

The present invention provides a new, improved and useful expendable electrode for electro-cardiographic measurements.

Expendable electrodes for electrocardiographic measurements have been known in the art. The previously known and available expendable electrodes of said applicability can be divided in two main groups, i.e. wet and dry electrodes operating, respectively, with and without a contact gel.

Wet expandable electrodes are supplied to the market without the contact gel and must be provided with a selected gel prior to being used, i.e. before their clamping or taping onto the skin. The contact gel is needed for bridging over the extremely high resistance of the epidermal corner layer of the skin. Applying the gel is a time-consuming operation and the duration depends on the selection of the gel and on the skill of the operator. To avoid the drawbacks connected with the known wet expendable electrodes, recently attempts have been made to provide them with an appropriate gel already placed thereupon. These electrodes however prove to have the drawback that the gel usually dries too quickly, so that in spite of the existing layer of gel, they must be, notwithstanding, provided with fresh gel layer. Besides, expendable electrodes of this construction are extremely expensive.

To avoid the above drawbacks and insufficiencies, dry expendable electrodes have been suggested. These comprise an integrated "FET" amplifier. The latter is an electrode having such a high impedance that the resistance of the epidermal corner layer is negligible. This, however, makes this electrode so expensive that it can be used only in very special cases where the cost does not play any considerable role.

A more recent attempt at providing an improved electrode is seen, for example, in U.S. Pat. No. 3,505,993, wherein metallic pins are provided in an attempt to enable the electrode to adhere more closely to the skin. The electrode however is rigid and must be made to conform to particular body shapes. Therefore a plurality of such units are necessary for any one operation.

BRIEF SUMMARY OF THE INVENTION

The present invention provides an expendable electrode for electro-cardiographic measurements comprising a relatively easily pliable and flexible metallic carrier member, such as a metallic thin plate or a mesh, preferably made of aluminum. The sheet-like carrier member is shaped to form on its outer surface a transverse flange preferably centrally positioned, projecting upwardly therefrom for contact with the lead wires to the electrocardiograph. On the side opposed to said flange, the carrier member is provided with an appropriate adhesive coating and with a plurality of regularly distributed metallic spikes devised to partially penetrate into the skin layers. In order to preserve the binding capacity of the adhesive coating and to protect the metallic spikes against outside influences and from any possible contamination, at least one removable sheet is placed over the carrier member surface bearing the adhesive coating and the metallic spikes.

Preferably, the plurality of contact establishing spikes are uniformly distributed over said surface and project therefrom so that the spikes may be easily caused to penetrate uniformly into the skin when the electrode is applied to a patient.

A suitable material for the carrier member is either a thin metallic foil or a thin metallic mesh network made of aluminum material.

The expendable electrode according to the present invention may be manufactured by forming a metallic carrier member in the form of either a thin plate or foil or a thin metallic mesh network, coating same on the side of its intended application to the skin with a layer of an adhesive compound and with a plurality of contact spikes projecting therefrom. For embedding said spikes, where a metallic carrier plate is used, the plate is suitably perforated to have formed therethrough uniformly distributed holes spaced apart one from the other at about 0.1 inch. Thereby a die may be used having obliquely cut steel pins with a diameter of about 0.6mm and cut at an angle of 30° relative to the axis of the pins. Thereafter, the spikes are inserted through said holes.

The carrier member also may be formed as a metallic thin mesh network. In this case, similarly as in that where a metallic plate is used, the network is provided with a coating of an adhesive compound on the surface which is intended to be applied to the corresponding area of the skin, on which surface the spikes are arranged. The spikes may be made from the wire wherefrom the mesh network itself is woven.

It is therefore an object of the present invention to provide for electro-cardiographic measurements and examinations an improved expendable electrode overcoming the shortcomings of the known both wet and dry electrodes available for similar use.

It is another object of the present invention to provide an expandable electrode of the above mentioned nature which is easily applied in practical application to the skin and which may be reshaped when used to be conformed both to flat and bowed portions of the body such as the various areas of the leg, arm or chest.

Still another object of the present invention is to provide an expendable electrode for electro-cardiographic measurements whose use does not require the application of any gel to the surface before application to the skin.

An additional object of the present invention is to provide an expendable electrode of the kind mentioned herein above comprising on the side of its application to the skin at least one pull-off sheet dimensioned and capable to protect both the adhesive against degradation and the spikes against harmful infectious soiling.

These and other objects and advantages and properties of the expendable electrode for electro-cardiographic measurements according to the present invention and its usefulness will be more fully described with reference to the accompanying drawings.

BRIEF DESCRIPTION OF THE DRAWINGS

In the accompanying drawings:

FIG. 2 shows another embodiment of the expendable electrode according to the present invention in a perspective view similar to that illustrated by FIG. 1, in which embodiment the metallic carrier member is a mesh network whose wires provide at the same time the contact spikes.

DETAILED DESCRIPTION OF THE INVENTION

Figure 1:
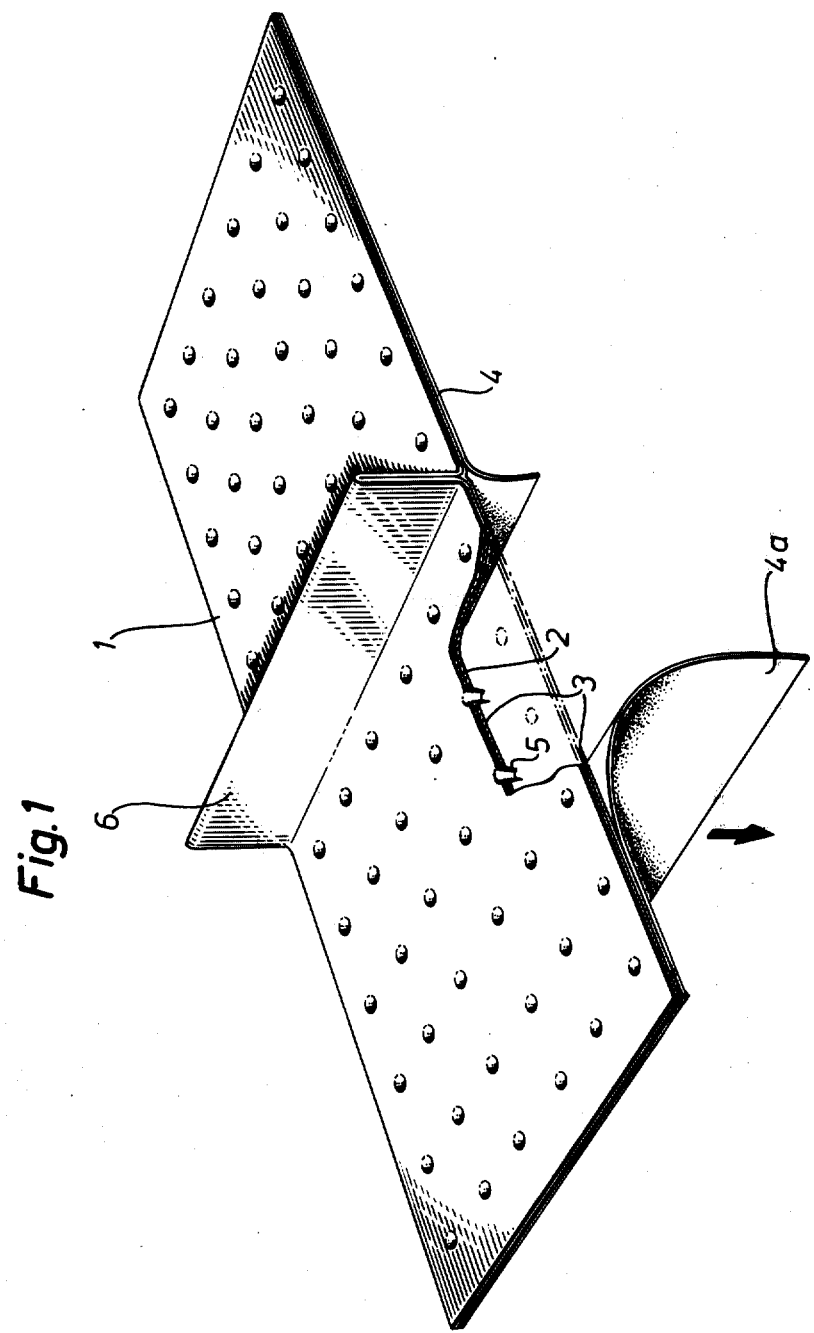
FIG. 1 is a perspective view of one exemplary embodiment of the expendable electrode for electro-cardiographic measurements according to the present invention, wherein there is shown a metallic carrier plate in partionally sectioned representation, as well as a covering pull-off sheet partially torn and peeled from said plate.

FIG. 1 shows an expendable electrode manufactured and constructed in accordance with the present invention, comprising a self-supporting thin aluminum foil 1 covered on its lower side 2, i.e. on the side intended to contact the skin, with a coating 3 made of an adhesive compound of the type commonly employed for removable contact with the skin. The foil 1 is provided with a plurality of regularly distributed spikes 5 of a conductive metal projecting from the lower side 2. These spikes 5 are joined to the aluminum foil 1 by perforating the foil with holes and thereafter inserting the spikes. Over said coating 3, one or two pull-off covering foils 4 and 4a are placed which are thick enough to entirely embed the spikes 5. The foil 1 is shown as being folded double and provided on the upper layer thereof with a transverse upwardly directed flange 6 designed to be coupled to conventional contact means of the electrocradiograph which FIG. 1 does not show.

The expendable electrode illustrated in FIG. 1 may be produced in the following manner:

An aluminum plate of the thickness of about 100 m$\mu$ is coated over the portion of its surface intended to form the area of contact with the skin with an acrylic adhesive compound to form thereupon a layer of dry adhesive 100 m$\mu$ thick. The aluminum plate is then perforated to form holes uniformly spaced from one another at about 0.1 inch. The piercing of the plate may be made by a die having obliquely cut steel pins of the diameter of about 0.6mm and cut at an angle of 30° in regard to the axis of the pins. This die is pressed through the coated portion of the aluminum plate to provide holes for spikes which are arranged to protrude from the plate a distance of about 400 – 500 m$\mu$. Then the aluminum plate is folded in a manner such that in the middle of its upper portion a transverse upwardly directed flange is formed, which flange serves as an element for attachment of the electrode to an electrocardiographic apparatus, the attachment being made for instance by clamping thereover a crocodile clip.

In practical experiments, the expendable electrode manufactured and constructed in accordance with the present invention has proved to be very easily applied to any desirable position on the body and is easily shaped to conform to an area of the skin subjected to examination. The layer of the adhesive compound also has shown to be very advantageous as a means for fixation of the electrode to the skin, since the entire surface of the metallic plate may be easily and satisfactorily brought in contact with any area of the skin where the measurement is to be carried out. The expendable electrode according to the present invention has a variety of utility which was not achievable by the respective electrodes known hitherto due either to their fixed non flexible shapes and/or to the fact that they had to be attached to the body either by taping, clamping and/or with use of a large amount of gel. The known electrodes also provided a poor contact with the skin surface which is overcome with the present invention.

Another embodiment of the present invention is displayed by FIG. 2 Here, the carrier member is formed as a metallic diamond mesh network, provided also with a coating of an adhesive compound on the surface to be applied to the skin and having a number of spikes projecting from this surface. The electrode in this embodiment is formed of a metallic diamond mesh network 1 which is made of brass wire or some other electrically conductive material which is inert to the body tissues. The mesh or diamond size is woven in conventional manner with preferably a 0.1 – 1 mm space between the wires. The lower side 2 of the mesh network 1 is covered by a coating 3 deposited from an adhesive material and the coating is also covered by a pair of removable foils 4 and 4a. From the lower side of the mesh network 1 and through the coating 3, contact spikes 5 are fed and erected. These contact spikes 5, having to penetrate into the skin when the electrode is applied thereto, are provided by cutting the wire in appropriate places of the mesh network and thereafter bending the wire downwardly throughout the coating 3. Thus, the contact spikes 5 constitute an integral part of the mesh metallic network. Also in this embodiment of the present invention, a double fold made on the upper layer of the network provides a transverse upwardly directed flange 6 forming a contact means for attachment to an electrocradiograph, not shown in FIG. 2.

The invention is of course not limited to the two embodiments shown in the drawings and described in connection therewith. The expendable electrode according to the present invention may be varied in many ways without departing from the scope thereof. Thus, for example, the contact flange can be provided on a place and in a manner other than as and where the flange is shown. Also for instance, the contact spikes may be provided so that they protrude, at least partially, from the adhesive coating for ensuring an effective penetration into the skin. The present disclosure is therefore to be taken as illustrative only of the present invention.

What is claimed is:

1. An expendable electrode for electrocardiographic measurements comprising a thin pliable metallic sheet-like carrier member adaptable to flexibly conform to the shape of the body part on which it is to be applied and having means for attachment of means for conducting signals from said carrier member to electrocardiographic equipment, said carrier member having one side adapted to be applied to the body part and another side facing away therefrom, said one side being provided with a plurality of regularly distributed spikes devised to penetrate into the skin and a coating of an adhesive compound adapted to adhere to the body, said coating and spikes being completely covered by at least one pull-off protective foil thick enough to entirely embed said spikes.

2. The expendable electrode according to claim 1, wherein said carrier member is a thin metallic plate.

3. The expendable electrode according to claim 2, wherein said spikes are separable from said plate.

4. The expendable electrode according to claim 2, wherein said metallic plate is made of aluminum.

5. The expendable electrode according to claim 1, wherein said spikes are made of a highly electrically conductive material.

6. The expendable electrode according to claim 1, wherein said carrier member is a metallic mesh.

7. The expendable electrode according to claim 6, wherein the spikes are formed by wires cut off said mesh, bent out and erected to project from said mesh into said coating.

8. The expendable electrode according to claim 7, wherein said wire forming said mesh is a highly electrically conductive metal.

9. The expendable electrode according to claim 1 wherein said means for attachment of said means for conducting signals comprises a flange directed upwardly from said another side of said sheet-like carrier member.

10. The expendable electrode according to claim 9 wherein said flange is formed by bending said sheet-like carrier member into a fold.

11. A method of manufacturing expendable electrodes for electrocardiographic measurements, comprising the steps of providing a thin pliable conductive sheet-like carrier member adapted to flexibly conform to the shape of the body to which it will be applied, providing on said carrier member means for attachment of means for conducting signals from said carrier member to electrocardiographic equipment, providing one face of said carrier member with a plurality of spikes regularly distributed thereover, depositing thereover a coating of an adhesive compound and completely covering said coated and spiked face of the carrier member with at least one protective pulloff foil entirely embedding said spikes.

12. The method according to claim 11, comprising the step of making said carrier member in the form of a thin metallic plate.

13. The method according to claim 12, comprising the step of forming said metallic plate as a relatively thin aluminum foil.

14. The method according to claim 13, comprising the step of forming said aluminum plate in the thickness of between 80 and 200 m$\mu$.

15. The method according to claim 12, comprising the steps of providing a die having obliquely cut steel pins of the diameter of 0.6 mm, cut at an angle of 30° to the axis of the pins and spaced from one another at 0.1 inch, perforating by these pins of said die the metallic plate to form holes therethrough and inserting into said holes the spikes to extend into said coating.

16. The method according to claim 11, comprising the steps of making said carrier member in the form of a thin diamond network, cutting the wire of said network in regularly distributed places and bending the cut-off portions of the wire to project from the network on the side of and into said coating, thus forming said spikes integral with said network.

17. The method according to claim 11, comprising the step of using an acrylic adhesive compound to form said coating and forming said coating in the thickness of between 80 and 200 m$\mu$.

18. The method according to claim 11 wherein the step of providing means for attachment of means for conducting signals comprises the step of forming a flange on the face of said sheet-like carrier member opposite said spiked face.

19. The method according to claim 9 wherein the step of providing means for attachment of means for conducting signals comprises the step of folding said sheet-like carrier member to form a flange extending across the face of said carrier opposite said spiked face.

* * * * *